Figure 1:
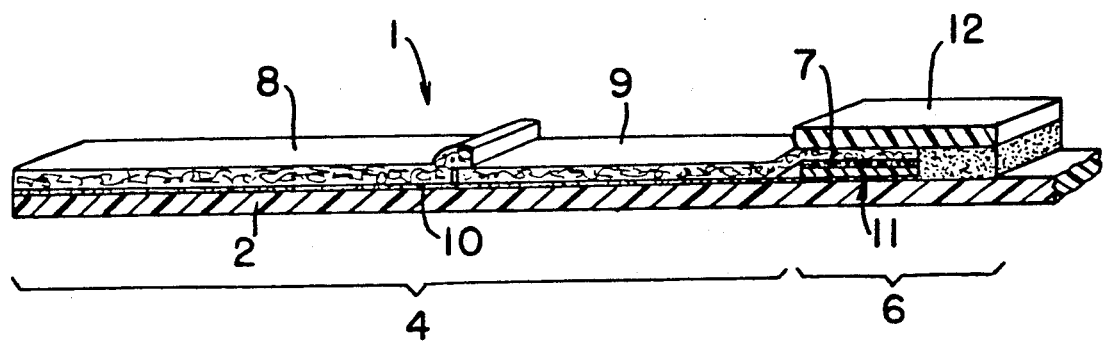

United States Patent [19]

Schlipfenbacher et al.

[11] Patent Number: 5,110,550
[45] Date of Patent: May 5, 1992

[54] TEST CARRIER FOR THE ANALYTICAL DETERMINATION OF A COMPONENT OF A LIQUID SAMPLE

[75] Inventors: Reiner Schlipfenbacher, Lampertheim; Joachim Steinbiss, Lorsch, both of Fed. Rep. of Germany

[73] Assignee: Boehringer Mannheim GmbH, Mannheim, Fed. Rep. of Germany

[21] Appl. No.: 384,726

[22] Filed: Jul. 25, 1989

[30] Foreign Application Priority Data

Jul. 30, 1988 [DE] Fed. Rep. of Germany ....... 3826057

[51] Int. Cl.⁵ .............................................. G01N 21/00
[52] U.S. Cl. ........................................ 422/56; 422/57; 422/58; 435/805
[58] Field of Search .................. 422/55, 56, 57, 58, 422/59, 60; 435/805

[56] References Cited

U.S. PATENT DOCUMENTS

| | | | |
|---|---|---|---|
| 4,275,031 | 6/1981 | Fischer et al. | 422/58 X |
| 4,292,916 | 10/1981 | Bradley et al. | 422/56 X |
| 4,477,575 | 10/1984 | Vogel et al. | 422/56 X |
| 4,618,533 | 10/1986 | Steuck | 428/315.7 |
| 4,780,280 | 10/1988 | Berger et al. | 422/58 X |
| 4,780,411 | 10/1988 | Piejko et al. | 422/56 |
| 4,820,644 | 4/1989 | Schäfer et al. | 422/55 X |
| 4,839,297 | 6/1989 | Freitag et al. | |
| 4,851,210 | 7/1989 | Hewett | 422/57 X |
| 4,861,711 | 8/1989 | Friesen et al. | |
| 4,891,313 | 1/1990 | Berger et al. | 435/7.94 |

FOREIGN PATENT DOCUMENTS 0256806 2/1988 European Pat. Off. .
3643516 6/1988 Fed. Rep. of Germany .

Primary Examiner—Robert J. Warden
Assistant Examiner—Arlen Soderquist
Attorney, Agent, or Firm—Felfe & Lynch

[57] ABSTRACT

A test carrier for the analytical determination of a component of a liquid sample, especially for the diagnosis of diseases, by means of a reaction sequence taking place on the test carrier with several test layers, which, in the initial state, are dry and, in the case of using the sample liquid, are wetted, comprising a base layer on which are present next to one another a sample application region and an evaluation region, a liquid transport path which extends from the sample application region into the evaluation region and a color-forming layer in which, on the basis of a color-formation reaction with the help of a color-forming reagent system, at least one color-forming reagent of which is present in the color-forming layer, there takes place an optically detectable change characteristic for the component to be determined. In the evaluation region above the surface of the color-forming layer facing away from the base layer, there is arranged an absorbent covering layer which, in the initial state of the test carrier, is so non-transparent that the color of the color-forming layer is not visible. The covering layer is in fluid contact with the liquid transport path and the covering layer and the color-forming layer are formed in such a manner that the color of the color-forming reagent becomes visible when both layers are wetted by the sample liquid.

11 Claims, 1 Drawing Sheet

TEST CARRIER FOR THE ANALYTICAL DETERMINATION OF A COMPONENT OF A LIQUID SAMPLE

The present invention is concerned with a test carrier for the analytical determination of a component of a liquid sample, especially for the diagnosis of diseases, by means of a reaction sequence taking place on the test carrier. The test carrier has several test layers. These comprise a base layer on which are present next to one another a sample application region and an evaluation region. A liquid transport path extends from the sample application region into the evaluation region. Furthermore, the test carrier has a color-forming layer in which, on the basis of a color-forming reaction, with the help of a color-forming reagent system, of which at least one color-forming reagent is present in the color-forming layer, there takes place an optically detectable change characteristic for the component to be determined.

For qualitative or quantitative analytical determinations in the scope of the diagnosis of diseases, in recent times so-called carrier-bound tests have been used to an increasing extent. In the case of these, reagents are embedded in corresponding layers of a solid test carrier which is brought into contact with the sample. The sample is usually a body fluid, for example blood or urine. However, it can also be a liquid obtained by a preceding test step, for example by contacting an elution agent with a faecal sample.

The reaction of the liquid sample with the reagents leads to a detectable signal, the present invention being concerned with cases in which there is produced a color change, which takes place in the color-forming layer and is characteristic for the component to be determined. The color change can be evaluated visually or by means of an appropriate apparatus, usually reflection photometrically.

Various color-forming reactions are used which consist of several reaction steps in which several different reagents participate. These are, in all, referred to as a color-forming reagent system. At least one color-forming reagent of this system is present in the color-forming layer and takes part in a reaction step which leads to the color change.

Test carriers are known in many different embodiments. They frequently have the form of a test strip which has one or more test fields on a longitudinal base layer. The test fields in turn frequently consist of several test layers which are of the same size and arranged above one another so that the sample liquid applied to the test field trickles through these vertically to the surface of the test layers. Since, in this case, the liquid transport takes place exclusively at right-angles to the test layer surfaces (and to the base layer), such test carriers can be referred to as "transverse transport test carriers".

The present invention is directed to "test carriers with longitudinal transport". As a rule, they have a longitudinally extending base layer on which a differentiation can be made between a sample application region and an evaluation region. In the case of such test carriers, the sample is applied to the sample application region and then transported along a liquid transport path, which runs parallel to the base layer, into the evaluation region. In comparison with transverse transport with test layers exclusively arranged above one another, such test carriers have considerable advantages and are, in particular, well suited for immunological analysis processes. The liquid transport is based upon capillary action, whereby the liquid transport path can be formed not only by one or more test layers of absorbent material, for example paper or fleece, but also by a gap which is sucked full by capillary action. Test carriers with longitudinal transport are described, for example, in published Federal Republic of Germany Patent Applications DE-A 34 45 816, DE-A 36 38 654 and DE-A 36 43 516.

It is important for the exactitude and dependable function of analysis test carriers that all test layers are wetted to a sufficient extent with sample fluid. On the other hand, in order to simplify handling, it should not be necessary to measure precisely the amount of sample liquid before application to the test carrier.

In the case of the known test carriers, the sample is usually applied in excess and then the user waits until the test carrier has absorbed completely. Whether or at what point of time this has actually taken place can usually not be monitored. According to the instructions for use, the user is simply to wait a particular period of time and thereafter remove the excess of sample, for example by wiping off or washing off.

Published European Patent Application EP-A 0,256,806 describes a transverse transport test carrier in which the base layer has an opening below the test field, the sample being applied from the other side to the test field. The opening serves the purpose of being able to observe the rear side of the test field reflection photometrically. The point of time at which the test field is completely wetted is thereby ascertained. However, this process is limited to transverse transport test carriers. The spreading out of the fluid over the surface of the test layer can only be monitored in a small partial region in which the opening is present and the possibility of monitoring is limited to cases in which the sample liquid is colored so that it can be detected directly.

It is an object of the present invention to provide a test carrier with which it is possible to monitor in a test carrier with longitudinal transport of the initially described type whether or at what point of time the test layers of the test carrier are properly wetted up to the color-forming layer and thus to improve the dosaging of the sample to the test carrier.

In accordance with the invention, a test carrier for the analytical determination of a component of a liquid sample, especially for the diagnosis of diseases, by means of a reaction sequence taking place on the test carrier, the test carrier comprises a) a base layer on which are located a sample application region and an evaluation region, b) a liquid transport path which extends from the sample application region into the evaluation region and c) a plurality of test layers which in the initial state before use are dry and are wetted in use by the sample liquid. The test layers comprise a) a color-forming layer having a surface facing away from the base layer and containing at least one color-forming reagent of a color-forming system and in which a color is formed by means of a color-formation reaction involving the color-forming reagent system. The test layers also include b) an absorbent covering layer arranged in the evaluation region above the surface of the color-forming layer facing away from the base layer, which in the initial state of the test carrier, is so non-transparent that the color of the color-forming layer is not visible therethrough. The covering layer is in fluid contact with the liquid transport path. The covering layer and the color-forming layer are so constructed and arranged that the color of the color-forming reagent becomes visible when both layers are wetted by the sample liquid.

As initial state is designated the "dry" state of the test carrier before application of the sample.

The term "fluid contact" is a designation which has become usual in test carrier technology for the case in which two test layers are so arranged with regard to one another that a liquid exchange is possible between them, usually on the basis of the sucking action of the test layers. The test layers can thereby be in direct contact with one another or the fluid contact can be brought about indirectly, for example via absorbent layers lying therebetween.

The covering layer consists of an absorbent material. There can be used, for example, paper, a textile material (fabric or fleece) or a porous synthetic material layer. Every such material has gaps or pores in which the liquid can be transported by capillary force.

Between the covering layer and the color-forming layer there should be laminar planar contact. Both layers can be connected with one another insofar as the liquid exchange is not thereby influenced to a disturbing extent. Preferably, however, they lie loosely on one another and are pressed against one another in appropriate manner, for example by a holding-down layer.

Important for the present invention is the cooperation of the longitudinal transport of the liquid and the making visible of the point of time at which the longitudinal transport is concluded. When the test carrier in the sample application region is brought into contact with the sample, this flows along the test carrier up to the detection region. This procedure is largely independent of the amount of sample applied so long as it only suffices for the complete wetting of all test layers. According to the present invention, there is now signalled the point of time of the complete filling of the test carrier. There is thereby not only possible a monitoring of the satisfactory function but also, in many cases, an improvement of the reproducibility of the liquid dosing is achieved.

In order that the color of the color-forming layer becomes visible when the covering layer and the color-forming layer are wetted with sample liquid, it is advantageous to make the color-forming layer such that the color-forming reagent, when wetted by the liquid, dissolves or disperses in this liquid and is thereby converted into a liquid state. The color-forming reagent can thereby penetrate into the covering layer so that its color becomes visible. In this case, the color-forming reaction preferably takes place preponderantly in the covering layer so that the change of the color can be readily observed or measured reflection photometrically.

A color-forming layer with a readily soluble color-forming reagent can be produced by impregnation of a carrier matrix. Since the sample liquid first spreads out in the covering layer laterally (parallel to the layer surface), the problem can, however, thereby arise that a rapidly soluble color-forming reagent enriches in the progressing liquid front and thereby brings about a non-homogeneous color formation.

In order to avoid this, the rate of liquid transport in the covering layer and the chronological commencement of the color-forming reaction in the color-forming layer are to be adapted to one another in such a manner that the liquid first spreads out in the covering layer and the color-forming reaction takes place substantially thereafter.

For this reason, the color-forming layer is preferably so constructed that the color-forming reagent is liberated with delay. This can be brought about by a delayed solubility of the color-forming reagent itself. Preferably, however, the delayed liberation is achieved in that the color-forming reagent is embedded in a film layer soluble with delay, which is present on a base layer made from a synthetic foil or a fabric.

According to an especially preferred embodiment, the color-forming reagent itself is more rapidly soluble than the film layer in which it is embedded. It is thereby achieved that the color-forming reagent, when it has been liberated from the signal-forming layer, reacts quickly and homogeneously in the liquid phase.

It is obvious that, in spite of the delaying of the color-formation reaction, this already starts to a small extent while the liquid is still spreading out in the covering layer. However, it is sufficient, if the color-forming reaction, in the sense of "substantially" takes place after the liquid spreading out, that a homogeneous signal formation is achieved on the whole of the signal-forming layer.

In order to bring about the desired retarded dissolving behavior, the color-forming layer preferably contains swellable macromolecules and/or a hydrophobic film former.

Swellable macromolecules in this sense are also referred to as hydrocolloids. These are macromolecular hydrophilic substances which are soluble in water or at least dispersable or swellable therein. These include especially polysaccharides, for example exudates (such as gum arabic), seed meals (such as carob bean meal and starch), extracts of plants (such as pectins and alginates), microbial polysaccharides(such as xanthan gum) and chemically modified polysaccharides (such as cellulose derivatives).

Certain proteins are also to be included in this group of substances, for example scleroproteins and hydrolysates thereof (for example collagen and crotein C), sparingly soluble reserve proteins (for example zein and precipitated casein) and hydrophobic drying proteins in correspondingly high concentrations (for example serum albumin).

As hydrophobic film formers in the sense of the present invention are to be understood water-soluble proteins which, in the case of drying from an aqueous solution, form a retardedly dissolvable film in which, due to the adhesive action of the polymers, the film content materials are fixed and bound.

The dissolving properties of such films can be controlled to a wide extent by choice of the polymers. These include, for example, polyvinyl alcohols, such as are commercially available under the trademark MOWIOL from Hoechst A.G. Frankfurt, Federal Republic of Germany (FRG), polyethylene oxide, such as is commercially available under the trademark POLYOX from the Union Carbide Corporation, New York, U.S.A. or acrylic resins, such as are obtainable from the firm Roehm, Darmstadt, FRG under the trademark EUDRAGID.

A second preferred measure in order to make the color of the color-forming reagent visible through the covering layer consists in producing the covering layer from a material which is opaque in a dry state but transparent in a moist state. The term "opaque" is thereby to be understood to mean that the layer is so substantially non-transparent that the color of the color-forming layer cannot be seen or only very weakly. It is decisive that there is a distinct difference in the transparency between the dry and the moist state.

A synthetic material membrane, i.e. a fine-pored synthetic resin layer, has proved to be an especially suitable material for the covering layer. A distinct difference with regard to transparency in the moist and dry state is shown by hydrophilic polyvinylidene difluoride, as is described in U.S. Pat. No. 4,618,533. However, on the basis of the present description, the expert can also select other materials and especially synthetic material membranes which fulfil the above-mentioned conditions. It is believed that the refractive index of the synthetic material is of major influence to this. It is to be assumed that porous materials, the refractive index of which is close to that of the sample liquid, have the property of becoming transparent in a moist state.

It is especially advantageous when a covering layer which is transparent in a moist state is used in combination with a soluble color-forming reagent penetrating from the color-forming layer into the covering layer.

For a better understanding of the invention, together with other and further objects thereof, reference is made to the following description taken in connection with the accompanying drawings, and its scope will be pointed out in the appended claims.

Figure 2:
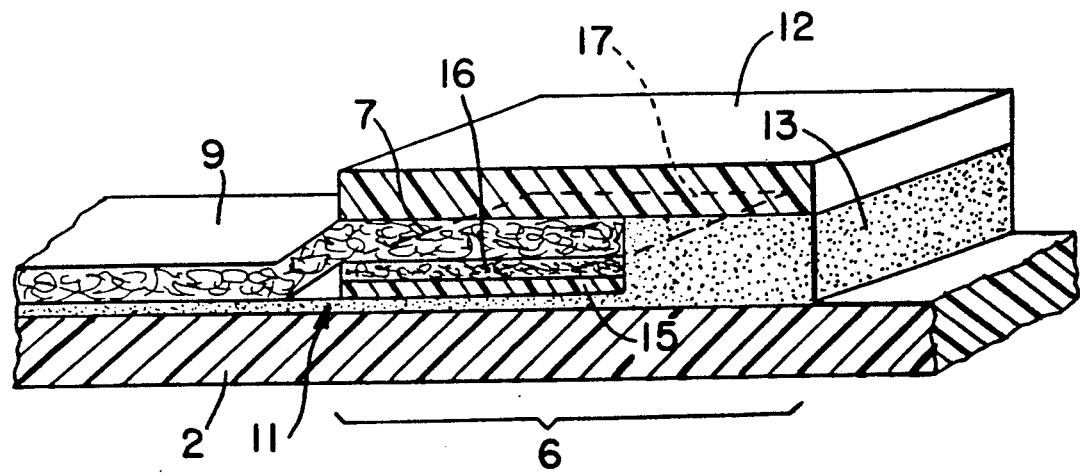

The present invention is especially suitable for a test for carrying out immunological determinations such as is explained in more detail in the following on the basis of an embodiment illustrated schematically in the accompanying drawings, in which:

FIG. 1 is a perspective view of a test carrier according to the present invention; and FIG. 2 is a fragmentary, detailed view to an enlarged scale, of the test carrier FIG. 1.

The test carrier 1 illustrated in the FIGS. has a base layer 2 on to which are fixed the other test layers. In its longitudinal direction, the test carrier can be subdivided into a sample application region 4 and an evaluation region 6. In the sample application region 4, there are fixed next to one another, by means of a melt adhesive 10 a conjugate layer 8 and a liquid transport layer 9 on the base layer 2. The layer 8 overlaps slightly the subsequent layer 9 in order to ensure a fluid contact between them which is as good as possible. The layers 8 and 9 form a liquid transport stretch which extends from the sample application and pre-reaction region 4 into the evaluation region 6.

In the illustrated example, the sample is applied to the conjugate layer 8, this layer thereby simultaneously serving for carrying out a first reaction state. The sample application region 4 simultaneously serves as pre-reaction region.

In the evaluation region 6 are to be seen on the base layer 2, as can be seen more clearly in FIG. 2, over one another a color-forming layer 11, a covering layer 7 and a holding-down layer 12. The holding down layer 12 consists of a comparatively stiff synthetic material film. By means of a melt adhesive strip 13 of appropriately great layer thickness, it is fixed to the base layer 2 in such a manner that it runs parallel thereto at a distance which corresponds approximately to the total thickness of the color-forming layer 11 and covering layer 7. The holding-down layer 12 has a sufficient stiffness in order to press together the layers present between it and the base layer 2 in such a manner that a good fluid contact is ensured between them.

In the case of the illustrated preferred embodiment, no further absorbent layers are provided beside the color-forming layer on its side facing away in the longitudinal direction of the base layer 2 from the sample application region 4 (thus in FIG. 1 on the right of the color-forming layer 11) there. Thus, the color-forming layer 11 is in fluid contact with the last section of the liquid transport path 8, 9, 7 in the liquid transport direction.

In the illustrated preferred embodiment, the color-forming layer 11 consists of a base film 15 and a film layer 16 of delayed solubility present thereon which contains a color-forming reagent.

As mentioned, the test carrier illustrated in the FIGS. is especially suitable for immunological determinations. Such determinations use highly specific binding reactions between different species which can be called binding partners. Immunological binding partners are, on the one hand, especially antibodies, as well as, on the other hand, antigens or haptens.

For the case in which an antigen AG contained in the sample is to be determined as analyte, the following course of the test is, for example, typical.

The sample is applied to the conjugate layer 8. The conjugate layer contains a soluble conjugate ABE of an antibody AB bindable specifically with the AG with an enzyme E. Complex AG-ABE results by the specific binding reaction.

Excess ABE passe together with the AG-ABE complex into the liquid transport layer 9. This contains an antigen AGF in carrier-bound form. The AGF is identical with the sample antigen or analogous to this, i.e. specifically bindable with the antibody of the ABE contained in the conjugate layer 8.

The excess free ABE is now carrier-fixed on the basis of the specific binding reaction with the antigen bound in the layer 9. To this end, it is important that the coating density of the fixed antigen on the layer 9 is high enough to ensure that practically the whole of the excess conjugate is bound thereon. Therefore, the layer 9 can also be referred to as "fixing layer". Only the free AG-ABE complexes pass into the evaluation zone 6. The amount of the AG-ABE complexes (and thus the amount of the labelling enzyme) thereby correspond to the amount of the analyte.

The sample liquid with the AG-ABE complexes flows further into the covering layer 7 and fills this completely substantially before the color-formation reaction with the color-forming reagent in the layer 11 commences. The delayed commencement of the color-formation reaction is, as described above, especially achieved in that the layer 11 dissolves retardedly.

The covering layer 7 is, as can be especially clearly recognized in FIG. 2, produced with the fixing layer 9 in one piece, i.e. both layers consist of a strip of the same material. This is preferred but not necessary. The covering layer 7 could also be a separate layer which is in liquid contact in any way with the liquid transport path 8, 9.

The liquid penetrates vertically to the layer surface uniformly through the liquid exchange surface 17 illustrated by broken lines in FIG. 2 into the color-forming layer 11. The color-forming layer 11 contains a substrate for the enzyme E. Depending upon the enzyme concentration, a color change takes place which is a measure for the concentration of the analyte.

The evaluation of the color change, visually or by means of apparatus, takes place from the side of the covering layer. So long as this is dry, it covers the color of the color-forming layer. After the covering layer has filled with liquid and the color-forming layer is wetted at least superficially, the color thereof is, on the contrary, visible. As explained hereinbefore, this can be achieved in that the color reagent passes over from the color-forming layer 11 into the liquid phase and passes further into the covering layer 7. In addition or alternatively, the covering layer can consist of a material which becomes transparent in the liquid state.

In a practical example, the color reagent is yellow colored in the initial state. The covering layer is non-transparently white so that the evaluation region appears to be white to the observer from the evaluation side. As soon as the covering layer is wetted with the liquid sample, the yellow color becomes visible. The observer can see from this that sufficient sample has been taken up and the longitudinal transport of the sample liquid in the test carrier has taken place satisfactorily. This color change can also be detected by means of apparatus. A fully automatic monitoring of the correct function of the test strip is thereby possible. The color change can be used for initiating a measurement procedure.

This monitoring function is independent of the coloration of the sample liquid. This is especially important when substantially colorless liquids are to be analyzed, such as urine or plasma.

As material for the covering layer and possibly also for the fixing layer 9 produced in one piece from the same material, there are especially suitable thin synthetic material membranes. The thickness of the material should preferably be less than 1 mm. and especially preferably less than 0.3 mm. The following materials are, for example, suitable:

BIODYNE BNRG (an ultrafiltration membrane on the basis of polyamide) of the firm Pall, Glen Cove, N.Y., U.S.A. 150 μm.

SM 119 of the firm Sartorius Göttingen, FRG, 140 μm.

Nitrocellulose of the firm Biorad, Richmond, Calif., U.S.A. 130 μm.

NC of the firm Schleicher & Schüll, Dassel, FRG, 150 μm.

The following materials, which are light-impermeably white in a dry state and are transparent in a moist state, are especially advantageous:

DURAPORE (an ultrafiltration membrane on the basis of polyvinylidine) and IMMOBILON (a "family" of surface active membranes for immobilizing biological active molecules), both produced by the firm Millipore, Bedford, U.S.A.

The manner of functioning of the test carrier has been described, by way of example, for the case in which an antigen is to be determined. An analogous course of the test is also possible for the determination of an antibody, an antigen conjugate then being used in the layer 8 and a carrier-fixed analogous antibody in the layer 9.

In general, the test carrier according to the present invention is especially suitable for those determinations in which the reaction sequence includes a specific binding reaction between a first binding partner (in the case of the example AG) correlated with the concentration of the component to be determined and a labelled second binding partner (in the case of the example ABE) with the formation of mobile complexes (in the case of the example AG-ABE) and a further specific binding reaction between the second binding partner (in the case of the example again ABE) and a third binding partner (in the case of the example AGF) carrier-fixed analogously to the first binding partner. It is thereby necessary that the second and the third binding partner, in each case referred to the direction of flow of the liquid, are arranged in the test carrier before the detection region thereof. The specific binding reaction is thereby concluded before the free complexes specific for the analysis pass into the detection region.

The described immunological course of the reaction is, apart from the peculiarities of the present invention, similar to that described in U.S. Pat. No. 4,839,297. Therefore, supplementary reference is made to this publication.

The test carrier according to the present invention is especially suitable as a detection unit for a test kit for the determination of an analyte in faeces, such as is described in published Federal Republic of Germany Patent Application DE-A 37 16 891. This test kit has a sample collecting unit, in which a liquid is obtained from the faecal samples by elution with the help of an elution agent, which liquid contains the analyte. The sample liquid thus obtained can advantageously be investigated with the test carrier according to the present invention.

The following Example is concerned with such a test carrier in which, as analyte, human serum albumin (hSA) is determined which has been eluted from a faecal sample and is an indicator for the presence of blood in faeces.

EXAMPLE

A test carrier according to FIGS. 1 and 2 of the accompanying drawings is produced as follows:

a) Conjugate layer 8:

IgG <human serum albumin> is covalently conjugated with $\beta$-galactosidase. This conjugate is impregnated into a glass fiber fleece and dried. The test layer size on the test carrier is 20×6 mm.

b) Fixing layer 9 and covering layer 7:

hSA is covalently fixed on to a membrane of hydrophilic polyvinylidene difluoride (PVDF) commercially available form the firm Millipore, Bedford, U.S.A. under trademark Immobilon AV. The surface concentration is adjusted via the concentration in the buffer used for the impregnation procedure to 20 μg. hSA/cm$^2$. The layer size is 20×6 mm.

c) Signal formation layer 11:

A film-forming coating mass is produced on the basis of 0.6% Ketrol F of the firm Kelco, Hamburg, FRG with the addition of 2.5% methylcellulose 15 of the firm Serva, Heidelberg, FRG. It contains 12 mM chlorophenol red-$\beta$-galactoside (CPRG) and is buffered in HEPES. The coating mass is coated in a film layer thickness of 200 μm. to a 100 μm thick carrier film of Pokalon of the firm Lonza, Weil/Rh., FRG. The layer size is 6×6 mm.

d) Holding layer 12:

This consists of a 140 μm. thick film of Pokalon.

As base layer, there is used a polyester film "Melinex" of the firm I.C.I., Frankfurt, FRG. The adhesion of the components takes place with the melt adhesive Dynapol S 1358 of the firm Dynamit Nobel, Troisdorf, F.R.G.

The liquid front moves comparatively slowly in the layer 9, 7 so that almost three minutes are needed up to the complete spreading out in the layer 7. Nevertheless, due to the retarded dissolving behavior of the substrate layer 11, there is achieved a completely homogeneous color formation depending upon the hSA concentration which permits a determination of this concentration with good exactitude.

The covering layer of the test carrier is initially white. Only when the liquid front has reached the covering layer, for which purpose about 180 seconds are needed, does a color change take place to yellow which indicates to the user that the sample liquid has spread out completely in the test carrier. The course of the color reaction can now be observed through the covering layer. In the case of this example, in the course of approximately a further 180 seconds, a color change to red takes place if an amount of human serum albumin lying above the sensitivity limit of the test is present in the sample.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Test carrier useful in determining a component of a liquid sample, comprising:
   (a) a base layer having positioned thereon,
      (i) a sample application region;
      (ii) an evaluation region;
   (b) a liquid transport path which extends from the sample application region into said evaluation region.
   (c) a plurality of test layers, comprising a color forming layer positioned in the evaluation region of said liquid transport path, said color forming layer having a surface facing away from said base layer and containing at least one color forming reagent, and
   (d) an absorbent covering layer positioned above said surface of the color forming layer facing away from said base layer, wherein said absorbent covering layer is in fluid contact with said liquid transport path, and said absorbent covering layer when wet permits visualization of color in said color forming layer but is non-transparent to, wherein the color forming layer and the absorbent covering layer are arraigned as the last section of the liquid transport path said color when dry.

2. Test carrier according to claim 1, wherein the absorbent layer consists of a material which is opaque in a dry state but is transparent in a moist state.

3. Test carrier according to claim 1, wherein the absorbent covering layer comprises a synthetic material membrane.

4. Test carrier according to claim 3, wherein the synthetic material membrane consists of polyvinylidene difluoride.

5. Test carrier according to claim 1, wherein the absorbent covering layer is less than 1 mm. thick.

6. Test carrier according to claim 5, wherein the absorbent covering layer is less than 0.3 mm. thick.

7. Test carrier according to claim 1, wherein the liquid transport path comprises a liquid transport layer which extends in one piece from the sample application region to over the whole color-forming layer simultaneously, forming the absorbent covering layer.

8. Test carrier of claim 1, further comprising (i) a mobile, labelled binding partner which specifically binds with the component to be detected or a substance which is indicative of said component, and (ii) a carrier bound binding partner which binds to any of said mobile labelled binding partner which does not bind to said component to be detected or said substance indicative of said component, wherein said mobile and carrier bound binding partners are positioned in said test carrier before said color forming layer.

9. Test carrier of claim 1, wherein said color forming reagent is dissolvably impregnated in said color forming layer.

10. Test carrier of claim 1, wherein said covering layer and said color forming layer comprise materials which permit spreading of said liquid sample in said covering layer before onset of reaction between said color forming reagent and a reactant transported thereto.

11. Test carrier of claim 1, further comprising a holding-down layer fixed on said base layer and having a liquid exchange surface region therebetween, whereby said color forming layer and covering layer are placed, pressed together, in said region.

* * * * *

UNITED STATES PATENT AND TRADEMARK OFFICE
CERTIFICATE OF CORRECTION

PATENT NO. : 5,110,550
DATED : May 5, 1992
INVENTOR(S) : Reiner Schlipfenbacher et al It is certified that error appears in the above-indentified patent and that said Letters Patent is hereby corrected as shown below:

Column 6, line 31: change "ABE passe" to --ABE passes--.

Column 8, line 45: change "from" to --form--.

Claim 1, line 20 (column 9, line 46): after "to" add --said color when dry--.

Claim 1, line 23, (column 10, line 3): delete "said color when dry".

Signed and Sealed this

Thirteenth Day of September, 1994

Attest:

BRUCE LEHMAN

*Attesting Officer*  *Commissioner of Patents and Trademarks*